United States Patent
Selvaganapathy et al.

(10) Patent No.: US 7,125,478 B2
(45) Date of Patent: Oct. 24, 2006

(54) MICROSCALE ELECTROPHORESIS DEVICES FOR BIOMOLECULE SEPARATION AND DETECTION

(75) Inventors: Ponnambalam Selvaganapathy, Fremont, CA (US); Mark A. Burns, Ann Arbor, MI (US); David T. Burke, Ann Arbor, MI (US); Carlos H. Mastrangelo, Bedford, NH (US)

(73) Assignee: The Regents of the University of Michigan, Ann Arbor, MI (US)

( * ) Notice: Subject to any disclaimer, the term of this patent is extended or adjusted under 35 U.S.C. 154(b) by 336 days.

(21) Appl. No.: 10/342,935

(22) Filed: Jan. 15, 2003

(65) Prior Publication Data
US 2003/0213693 A1 Nov. 20, 2003

Related U.S. Application Data

(60) Provisional application No. 60/349,602, filed on Jan. 18, 2002.

(51) Int. Cl.
*G01N 27/447* (2006.01)
*G01N 27/453* (2006.01)
*G01N 30/02* (2006.01)

(52) U.S. Cl. .................. 204/452; 204/603; 422/70; 73/61.58; 73/61.61

(58) Field of Classification Search ............... 422/70, 422/100; 204/600–605, 450–455; 73/61.58, 73/61.61
See application file for complete search history.

(56) References Cited

U.S. PATENT DOCUMENTS

| | | | |
|---|---|---|---|
| 4,683,195 A | 7/1987 | Mullis et al. | 435/6 |
| 4,683,202 A | 7/1987 | Mullis | 435/91 |
| 4,829,324 A | 5/1989 | Drake et al. | 346/140 R |
| 5,091,328 A | 2/1992 | Miller | 437/52 |
| 5,160,419 A * | 11/1992 | Kageyama et al. | 204/294 |
| 5,194,133 A * | 3/1993 | Clark et al. | 204/608 |
| 5,318,680 A * | 6/1994 | Fishman et al. | 204/453 |
| 5,670,031 A * | 9/1997 | Hintsche et al. | 205/777.5 |
| 6,057,149 A | 5/2000 | Burns et al. | 435/287.2 |
| 6,159,353 A * | 12/2000 | West et al. | 204/601 |

FOREIGN PATENT DOCUMENTS

FR 2672301 8/1992

OTHER PUBLICATIONS

Kirk-Othmer Encyclopedia of Chemical Technology, 4th ed., vol. 9, 1994, pp. 88-111.*
JPO English language translation of JP 2001-108655A (Niwa et al.), issued Apr. 20, 2001.*
Arnheim, "Polymerase Chain Reaction Strategy," *Annu. Rev. Biochem.* 61:131, 1992.
Brake, M.L., et al., "Reactive ion etching in the gaseous electronics conference RF reference cell," *J. Res. Natl. Inst. Stand. Technol.*, 100:441-448, 1995.
Doty et al., "Strand Separation and Specific Recombination in Deoxyribonucleic Acids:Physical Chemical Studies," *Proc.Nat. Acad.Sci., U.S.A.* 46:461-477, 1960.
Dussan, "On the Spreading of Liquids on Solid Surfaces Static and Dynamic Contact Lines," *Annual Review of Fluid Mechanics* 11:371, 1979.

(Continued)

*Primary Examiner*—Alex Noguerola
(74) *Attorney, Agent, or Firm*—Medlen & Carroll, LLP (57) ABSTRACT

The present invention relates to microfabrication and utilization of microscale electrophoresis devices as well as the separation and detection of biomolecules in microscale electrophoresis devices. The device of the present invention utilizes novel fabrication and detection methods.

11 Claims, 8 Drawing Sheets

OTHER PUBLICATIONS

Effenhauser, C.S., et al., "Manipulation of Sample Fractions on a Capillary Electrophoresis Chip," *Anal. Chem.* 67:2284-2287, 1995.

Gavin, P.F. and A.G. Ewing, "Continuous separations with microfabricated electrophoresis-electrochemical array detection," *J. Am. Chem. Soc.*, 118:8932-8936, 1996.

Gordon et al., "Capillary Electrophoresis," *Science* 27:224, 1988.

Graham et al., "Direct DNA sequencing using avian myeloblastosis virus and Moleney murine leukemia virus reverse transcriptase," Bethesda Res. Lab. Focus 8(2):4, 1986.

Hayashi et al., "Restriction of in Vivo Genetic Transcription to one of the Complementary Strands of DNA," *Proc.Nat.Acad.Sci., U.S.A.* 50: 664-671, 1963.

Heller and Tullis, "Microelectrophoresis for the separation of DNA fragments," *Electrophoresis* 13:512, 1992.

Hietpas, P.B., et al., "Ultrathin Slab Gel Separations of DNA Using a Single Capillary Sample Introduction System," *Anal. Chem.* 69:2292-2298, 1997.

Hunkapiller, M.W., "Advances in DNA sequencing technology," *Curr. Op. Gen. Devl.* 1:88-92, 1991.

Innis et al., "DNA sequencing with *Thermus aquaticus* DNA polymerase and direct sequencing of polymerase chain reaction-amplified DNA," *Proc. Natl. Acad. Sci. USA* 85:9436-9440, 1988.

Jorgenson and Lukacs, "High-Resolution Separations Based on Electrophoresis and Electroosmosis," *J. Chrom.* 218:209, 1981.

Kafil, J.B., et al., "Quantitation of nucleic acids at the picogram level using HPLC with electrochemical detection," *Anal. Chem*, 58:285-289, 1986.

Lawrence Berkeley Lab Presentation, Park City, Utah (1993).

Laing, Z., et al., "Microfabrication of Planar Absorbance and Florescence Cell for Integrated Capillary Electrophoresis Devices," *Anal. Chem.* 68:1040-1046, 1995.

Man, P.F., et al., "Microfluidic capillaries on silicon: A new inexpensive technology for bioanalysis chips," *IEEE MEMS 1997 Conference, Nagoya Japan*, pp. 311-316, 1997.

Manz, A., et al., "Electrophoresis Pumping and Electrophoresis Separations for Miniaturized Chemical Analysis Systems," *J. Micromech. Microeng.* 4:257-265, 1994.

Manz et al., "Planar chips technology for miniaturization and integration of separation techniques into monitoring systems Capillary electrophoresis on a chip," *J. Chrom.* 593:253, 1992.

Marmur and Lane, "Strand Separation and Specific Recombination in Deoxyribonucleic Acids: Biological Studies," *Proc.Nat.Acad. Sci., U.S.A.* 46:453-461, 1960.

Maxam and Gilbert, "A new method for sequencing DNA," *Proc. Natl. Acad. Sci. USA*, 74:560-564, 1977.

Mullis and Faloona, "Specific Synthesis of DNA *in Vitro* via a Polymerase-Catalyzed Chain Reaction," *Meth. Enzym.* 155:335, 1987.

Nickerson et al., "Automated DNA diagnostics using an ELISA-based oligonucleotide ligation assay," *Proc. Nat. Acad. Sci. USA* 87:8923, 1990.

Nowak, "Xeroxing DNA Analysis," *Science* 268:1135, 1995.

Pentoney et al., "A single-fluor approach to DNA sequence determination using high performance capillary electrophoresis," *Electrophoresis* 13:467-474, 1992.

J. Pfahler et al., "Liquid Transport in Micron and Submicron Channels," *Sensors and Actuators*, A21-A23, pp. 431-434, 1990.

Probstein, "Physicochemical Hydrodynamics," pp. 64-67, 300-315, 1989.

Presentation at Cold Spring Harbor, "DNA Amplification in Small Volumes," (Aug. 31-Sep. 2, 1995).

Rodriguez, M. and A.J. Bard, "Electrochemical studies of the interaction of metal chelates with DNA," *Anal. Chem.*, 62:2658-2662, 1997.

Sambrook, J. et al., Molecular Cloning, A Laboratory Manual, 2d Ed. Cold Spring Harbor Laboratory Press, New York, 13.7-13.9.

Sanger et al., "DNA sequencing with chain-terminating inhibitors," *Proc. Natl. Acad Sci. USA* 74:5463-5467, 1977.

R.F. Service, "The Incredible Shrinking Laboratory," *Science* 268:26-27, 1995.

Smits, "Piezoelectric Micropump with Three Valves Working Peristaltically," *Sensors and Actuators* A21-A23:203, 1990.

Southern, "Detection of Specific Sequences Among DNA Fragments Separated by Gel Electrophoresis," *J.Mol.Biol.* 98:503-517,1975.

Smith and Wilcox, "A Restriction Enzyme from *Hemophilus influenzae*," *J.Mol.Biol.* 51:379-391, 1970.

Tabor et al., "DNA sequence analysis with a modified bacteriophage T7 DNA polymerase," *Proc. Natl. Acad. Sci. USA* 84:4767-4771, 1987.

Tenan et al., "Friction in Capillary Systems," *Journal of Applied Physics* 53:6687, 1982.

Turner, "New Dimensions in Capillary Electrophoresis Columns," LC-GC vol. 9 (1991).

H.T.G. Van Lintel et al., "A Piezoelectric Micropump Based on Micromachining of Silicon," *Sensors and Actuators* 15:153-167, 1988.

Voegel, P.D. and R.P. Baldwin, "Electrochemical detection in capillary electrophoresis," *Electrophoresis*, 18:2267-2278, 1997.

Webster, J.R., et al., "Electrophoresis system with integrated on-chip fluorescence detection," *IEEE MEMS 2000 conference, Miyazaki, Japan*, pp. 306-310, Jan. 2000.

Woolley, A.T. and R.A. Mathies, "Ultra-high speed fragment separations using microfabricated capillary array electrophoresis chips," *Proc. Natl. Acad. Sci., USA*, 91:11348-11352, 1994.

Woolley, A.T. and Mathies, R.A., "Ultra-High-Speed DNA Sequencing Using Capillary Electrophoresis Chips," *Anal. Chem.* 67:3676-3680, 1995.

\* cited by examiner

MICROSCALE ELECTROPHORESIS DEVICES FOR BIOMOLECULE SEPARATION AND DETECTION

This application claims priority under 35 U.S.C. 119(e) from provisional application No. 60/349,602, filed Jan. 18, 2002.

FIELD OF THE INVENTION

The present invention relates to the fabrication and methods of use of a novel microscale, inline electrochemical detection system.

BACKGROUND

Capillary electrophoresis (CE) and other analytical techniques have greatly benefited from micromachining. Microfabrication technology provides a means for implementation of complex CE devices with a high degree of functionality (Woolley, A. T. and R. A. Mathies, "Ultra-high speed fragment separations using microfabricated capillary array electrophoresis chips", *Proc. Natl. Acad. Sci., USA*, 91:11348–11352, 1994; Bousse, L. et al., "High performance DNA separations in microchip electrophoresis systems", *Proc. micro-TAS '98 Workshop*, pp. 271–275, 1998) yielding fast and highly efficient separations. The majority of micromachined CE devices, however, have been fabricated using bonded, glass substrate technology with off-chip laser induced fluorescence detection. The advantages of miniaturization are greatly reduced when large detection systems are used in microanalysis.

A prior art method of on chip detection utilized a photodiode on silicon (Webster, J. R., et al., "Electrophoresis system with integrated on-chip fluorescence detection", *IEEE MEMS 2000 conference, Miyazaki, Japan*, pp. 381–385, January 2000). However, compatibility of the silicon photodiode with plastic substrates, which are favored because of bio-compatibility and cost, is difficult to achieve. Additionally, the optical detection method required additional optical devices such as LEDs, lasers and optical filters for efficient detection thereby increasing the systems bulk.

Electrochemical detection methods have also been tried in micromachined CE, however, the methods tried thus far have been end column methods. End column detection limits resolution (Voegel, P. D. and R. P. Baldwin, "Electrochemical detection in capillary electrophoresis", *Electrophoresis*, 18:2267–2278, 1997; Gavin, P. F. and A. G. Ewing, "Continuous separations with microfabricated electrophoresis-electrochemical array detection", *J. Am. Chem. Soc.*, 118:8932–8936, 1996). Inline electrochemical methods have been used in large scale HPLC, for example (Kafil, J. B., et al., "Quantitation of nucleic acids at the picogram level using HPLC with electrochemical detection", *Anal. Chem*, 58:285–289, 1986). However, inline electrochemical detection methods have not been employed in micromachined CE because of problems in coupling detection and separation fields and in bubble generation in aqueous solution at the high CE fields.

What is needed is an inexpensive, easy to fabricate electrochemical detection system that provides improved resolution and a higher limit of detection.

SUMMARY OF THE INVENTION

The present invention relates to microfabrication of microscale electrophoresis devices and the separation and detection of biomolecules in microscale electrophoresis devices. The present invention contemplates microscale capillary electrophoresis devices, comprising an electrochemical inline detection system, comprising: i) a substrate; ii) one or more electrophoresis microchannels on said substrate; iii) a sieving matrix disposed within said one or more channels; iv) one or more reservoirs in fluidic communication with said one or more channels; and v) a detector positioned inline with respect to at least one of said one or more channels, said detector comprised of first, second and third electrodes. In a preferred embodiment, the first electrode is a reference electrode, the second electrode is a detection electrode, and the third electrode is a counter electrode. In yet another embodiment, the detection is configured such that said reference electrode envelopes (e.g., surrounds or substantially surrounds) said working electrode. In still yet another embodiment, the substrate comprises a material selected form the group consisting of silicon, glass, plastic, metal, ceramics or quartz. The electrodes typically comprise a metal or metal salt. In one embodiment, the material selected for the electrode is from the group consisting of gold, silver/silver chloride, carbon, palladium or platinum. In still yet another embodiment, the detection system (e.g., the spacing of the working, counter and reference electrodes) is to be no more 150 μM in width. In a more preferred embodiment, the detection system is to be no more 100 μM in width. The most preferred embodiment, the detection system is to be no more 80 μM in width.

In a preferred embodiment, the present invention contemplates a detection system, wherein the detection system is inline. In another embodiment, the present invention contemplates a detection system, wherein the detection system is off-chip. In one embodiment, the off-chip detection system may be optical (e.g., detection of fluorescently labeled biomolecules).

In one embodiment the sieving matrix may be argarose, acrylamide, methyl cellulose, hydroxypropylcellulose, hydroxypropylmethyl cellulose, dextran or glucomannan. In a preferred embodiment, the sieving matrix is hydroxyethylcellulose (HEC).

The present invention further contemplates the device of the present invention where the device is in communication with microscale reaction devices (e.g., the devices of U.S. Pat. No. 6,057,149, incorporated herein by reference) or sample loading devices.

In a preferred embodiment, these elements are microfabricated on top of (or etched within) substrates or support platforms comprised of, e.g., silicon, glass, plastic, quartz, ceramics or metal. In one embodiment, the various components are linked together (i.e., in liquid or "fluidic" communication). In another embodiment, the various components are not linked (i.e., in liquid communication). In one embodiment, the various components are in liquid communication by using a surface-tension-gradient mechanism in which discrete droplets are differentially heated and propelled through etched channels. In another embodiment, the various components are in liquid communication by a continuous stream wherein the flow is regulated by valves and pumping. In yet another embodiment, the present invention contemplates the components of the present invention are in liquid communication by capillary action. In yet another embodiment, various electronic components (e.g., electrodes) are fabricated on the same support platform material, allowing sensors and controlling circuitry to be incorporated in the same device. Since all of the components are made using conventional photolithographic techniques, multi-component devices can be readily assembled into complex, integrated systems.

In one embodiment, the present invention contemplates a method of fabricating of a capillary electrophoretic device, comprising: i) providing: a) a support platform and, b) etching means; ii) applying a passivation layer to said support platform; iii) applying a base layer to said passivation layer; iv) applying first, second and third electrodes in a configuration for detection to said base layer; v) applying a photoresist layer to said base layer and said electrodes; vi) applying a top layer to said photoresist layer, said base layer and said electrodes; and, vi) removing said photoresist layer with said etching means to produce a capillary electrophoresis channel with an inline detector, said detector comprising said first, second and third electrodes. In another embodiment, the first electrode is a reference electrode, the second electrode is a detection electrode, and the third electrode is a counter electrode. In yet another embodiment, the reference electrode envelopes said working electrode. In yet another embodiment, the support platform comprises a material selected form the group consisting of silicon, glass, plastic, metal, ceramics or quartz. In still yet another embodiment, the passivation layer comprises thermal oxide. In still yet another embodiment, the base layer and top layer comprise parylene. In still yet another embodiment, the electrodes comprises a material selected form the group consisting of gold, silver/silver chloride, carbon, palladium or platinum. In still yet another embodiment, the detection system (e.g., the working, counter and reference electrodes) is to be no less more 150 μM in width. In a more preferred embodiment, the detection system is to be no less more 100 μM in width. The most preferred embodiment, the detection system is to be no less more 80 μM in width.

It has been found empirically that the methods and devices of the present invention can be used when, prior to the use of the fabricated microdevice described above the liquid transport channel (or channels) is treated with a hydrophilicity-enhancing compound. It is not intended that the invention be limited by exactly when the treatment takes place. Indeed, there is some flexibility because of the long-life characteristics of some enhancing compounds. In another embodiment, the liquid transport channel (or channels) are not treated with a hydrophilicity-enhancing compound.

The present invention is not limited to any particular material for the platform or housing. For example, silicon, glass, plastic, quartz, ceramics and metal may be used. In a preferred embodiment, silicon is used for the platform or housing.

The present invention is not limited to any particular material for the passivation layer. In a preferred embodiment, trichloroethane (TCA) is used.

The present invention is not limited to any particular material for the base layer or the top layer. In a preferred embodiment, parylene is used for the base layer and the top layer. Parylene is a conformal protective polymer coating material utilized to uniformly protect any component configuration on such diverse substrates as metal, glass, paper, resin, plastic, ceramic, ferrite and silicon. The present invention is not limited to the use of parylene for the base layer and top layer. Any conformal polymer or non-polymer may be used.

The present invention is not limited to any particular material for the photoresist layer. In a preferred embodiment, the photoresist is Microposit 1813 (Shipley Co.).

The present invention is not limited to any particular etching means or etching method. In one embodiment, the etching method is wet-etching. In a preferred embodiment, the etching method is oxygen plasma reactive-ion etching.

It is not intended that the present invention be limited by the nature of the substances detected in the microscale device. Substances include, but are not limited to, chemical and biological substances. Biological reactions include, but are not limited to products of sequencing, restriction enzyme digests, RFLP, nucleic acid amplification, proteins, peptides and amino acid chains. It is also not intended that the invention be limited by the particular purpose for carrying out the biological reactions. In one medical diagnostic application, it may be desirable to differentiate between a heterozygotic and homozygotic target and, in the latter case, specifying which homozygote is present. In another medical diagnostic application, it may be desirable to simply detect the presence or absence of specific allelic variants of pathogens in a clinical sample.

In one embodiment, the present invention contemplates a method comprising: i) providing: a) the device of Claim 1 wherein said device comprises electrophoresis channels comprising a sieving matrix, b) fluid comprising biomolecules and, c) a detection means; ii) applying said fluid comprising biomolecules to said sieving matrix and; iii) detecting said biomolecules with said detection means. In another embodiment, the present invention contemplates a method comprising: i) providing: a) the device of Claim 1 wherein said device comprises electrophoresis channels comprising a sieving matrix, b) fluid comprising biomolecules and, c) a potentiostatic detection means; ii) applying said fluid comprising biomolecules to said sieving matrix and; iii) detecting said biomolecules with said potentiostatic detection means.

In yet another embodiment, the present invention contemplates a method comprising: i) providing: a) the device of Claim 1 wherein said device comprises electrophoresis channels comprising a sieving matrix, b) fluid comprising biomolecules wherein said biomolecules are labeled and, c) a detection means; ii) applying said fluid comprising biomolecules to said sieving matrix and; iii) detecting said biomolecules with said detection means. In still yet another embodiment, the present invention contemplates that the biomolecules are fluorescently labeled.

DEFINITIONS

The following definitions are provided for the terms used herein:

"Biological reactions" means reactions involving biomolecules such as enzymes (e.g., polymerases, nucleases, etc.) and nucleic acids (both RNA and DNA). Biological samples are those containing biomolecules, such proteins, lipids, nucleic acids. The sample may be from a microorganism (e.g., bacterial culture) or from an animal, including humans (e.g. blood, urine, etc.). Alternatively, the sample may have been subject to purification (e.g. extraction) or other treatment. Biological reactions require some degree of biocompatability with the device. That is to say, the reactions ideally should not be substantially inhibited by the characteristics or nature of the device components.

"Chemical reactions" means reactions involving chemical reactants, such as inorganic compounds.

"Channels" are pathways through a medium (e.g., silicon) that allow for movement of liquids and gasses. Channels thus can connect other components, i.e., keep components "in liquid communication." "Microdroplet transport channels" are channels configured (in microns) so as to accommodate "microdroplets". While it is not intended that the present invention be limited by precise dimensions of the channels or precise volumes for microdroplets, illustrative ranges for channels and microdroplets are as follows: the channels can be between 0.35 and 50 µm in depth (preferably 20 µm) and between 50 and 1000 µm in width (preferably 500 µm), and the volume of the microdroplets can range (calculated from their lengths) between approximately one (1) and (100) nanoliters (more typically between ten and fifty). An "electrophoresis channel" is a channel substantially filled with a material that aids in the differential migration of DNA.

"Conveying" means "causing to be moved through" as in the case where a microdroplet is conveyed through a transport channel to a particular point, such as a reaction region. Conveying can be accomplished via flow-directing means.

"Flow-directing means" is any means by which movement of a microdroplet in a particular direction is achieved. A preferred directing means employs a surface-tension-gradient mechanism in which discrete droplets are differentially heated and propelled through etched channels.

"Hydrophilicity-enhancing compounds" are those compounds or preparations that enhance the hydrophilicity of a component, such as the hydrophilicity of a transport channel. The definition is functional, rather than structural. For example, Rain-X™ anti-fog is a commercially available reagent containing glycols and siloxanes in ethyl alcohol. However, the fact that it renders a glass or silicon surface more hydrophilic is more important than the reagent's particular formula.

"Initiating a reaction" means causing a reaction to take place. Reactions can be initiated by any means (e.g., heat, mixing of reagents, wavelengths of light, addition of a catalyst, etc.)

"Liquid barrier" or "moisture barrier" is any structure or treatment process on existing structures that prevents short circuits and/or damage to electronic elements (e.g., prevents the destruction of the aluminum heating elements). In one embodiment of the present invention, the liquid barrier comprises a first silicon oxide layer, a silicon nitride layer, and a second silicon oxide layer.

"Merging" is distinct from "mixing". When a first and second microdroplet is merged to create a merged microdroplet, the liquid may or may not be mixed. Moreover, the degree of mixing in a merged microdroplet can be enhanced by a variety of techniques contemplated by the present invention, including by not limited to reversing the flow direction of the merged microdroplet.

"Nucleic Acid Amplification" involves increasing the concentration of nucleic acid, and in particular, the concentration of a particular piece of nucleic acid. A preferred technique is known as the "polymerase chain reaction." Mullis, et al., U.S. Pat. Nos. 4,683,195 and 4,683,202, hereby incorporated by reference, describe a method for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segment of the target sequence become the dominant sequences (in terms of concentration) in the mixture, they are said to be "PCR-amplified."

"Microfabricated", "micromachined" and "micromanufactured" mean to build, construct, assemble or create a device on a small scale (e.g., where components have micron size dimensions) or microscale. In one embodiment, electrophoresis devices are microfabricated ("microfabricated electrophoresis device") in about the millimeter to centimeter size range.

"Microelectrode" means an electrode that was microfabricated on a small scale. In the context of the present invention, the microelectrode is small enough to load samples onto the microfabricated electrophoresis device of the present invention. For example, in one embodiment, the microelectrode of the present invention was fabricated by first depositing a 2000 521 thick layer of thermal oxide on the silicon wafer to provide electrical insulation. A positive photoresist (PR 1827, Hoechst Celanese) was applied, patterned and developed. A 300 Å thick titanium metal layer followed by a 2000 Å thick platinum metal layer was deposited on the substrate by electron beam evaporation. The resist and the overlying metal layers were then 'lifted off' by development using Microposit 1112A remover in solution (Shipley Co., Newton, Mass.). The wafers were then rinsed and dried. Microelectrodes may also be deposited on quartz and glass wafers using a similar process.

"Polyacrylamide (gel)" is a term understood by those practiced in the art to mean a gel that suppresses convective mixing of the fluid phase through which electrophoresis takes place and contributes molecular sieving. Polyacrylamide gels may be crosslinked or non-crosslinked.

"Crosslinked" means the linking of the chains of a polymer (e.g., polyacrylamide) to one another so that the polymer, as a network, becomes stronger and more resistant to being dissolved and permits better separation of sample components when used in electrophoresis. Bis-acrylamide is an example of a cross-linking agent used in polyacrylamide electrophoresis.

"Polymer" refers to a substance formed from two or more molecules of the same substance. Examples of a polymer are gels, crosslinked gels and polyacrylamide gels. Polymers may also be linear polymers. In a linear polymer the molecules align predominately in chains parallel or nearly parallel to each other. In a non-linear polymer the parallel alignment of molecules is not required.

"Sample injection means", "microelectrode sample injection means" or "microelectrode sample injection component" refer to the method or device used to load sample onto a polyacrylamide gel, e.g., by inserting the sample into the loading chamber and applying electric current in order to compact the sample. Details of the procedure are in Example 5. In the present invention the sample injection means is performed, e.g., using a microelectrode.

"Photodefined polyacrylamide gels" are polyacrylamide gels that are polymerized by exposure of at least a part of the gel to a light source. The unexposed part of the gel may then be removed (e.g., by washing) leaving a well defined sample loading surface.

"Injection plug" and "sample plug" refer to the sample deposited on the gel and concentrated by microelectrodes.

"Concentration," "concentrated" and "to concentrate a sample" and similar terms refer to the increase in density or packing of solutes in a sample by removing part of the liquid in the sample. For example, the electrophoresis samples of the embodiments of the present invention are concentrated by bringing together the solutes of the sample at an electrode and displacing the water or other liquids at the electrode until the sample is concentrated to about 50 microns or less.

"Micro-electrophoresis device" refers to a small (e.g., micron size components) scale device for performing electrophoresis. In one embodiment, it is contemplated that the micro-electrophoresis device comprises electrophoresis channels of about 400 μm or less (width) by 40 μm or less (depth).

"UV illumination" and "UV irradiation" shall refer to UVA illumination. In one embodiment of the present invention, the UVA illumination is from an "UVA illumination source", e.g., an Amersham ReproSet™ UV gel set box using a 40 watt mercury vapor bulb.

"Loading channel" refers to a channel in the electrophoresis device of embodiments of the present invention, wherein the gel and samples of the present invention are deposited.

"Shielding device" refers to a device designed to shield a portion of the gel from UVA illumination during photopolymerization.

"Passivation layer" shall refer to a layer of material applied to a substrate surface (e.g., a support platform) to reduce or eliminate the chemical and electrical reactivity of the surface and to protect against contamination by the surface.

"Substrate" shall refer to an underlying support layer (e.g., a support platform) on to which other materials are applied. The substrate or support platform may be made of any suitable material including, but not limited to, silicon, glass, plastic, quartz, resin, ceramics and metal.

"Base layer" shall refer to a layer of material applied to a support platform for the purpose of insulation, moisture proofing and to provide a compatible surface on which a reaction, assay or procedure (e.g., electrophoresis) may take place.

"Top layer" shall refer to a layer of material applied to the top side of a reaction chamber for the purpose of protection of the chamber, insulation, reducing moisture loss and to provide a compatible surface on which a reaction, assay or procedure (e.g., electrophoresis) may take place.

"Photoresist layer" shall refer to an expendable, removable layer of material that is used, for example, to create a chamber between two other layers or to protect the material under it from, e.g., etching.

"Etching means" shall refer to a process by which a material is cut into or through its surface.

"Applied" shall refer to when two or more substances, items, etc. are put into contact with each other.

"Analyte" shall refer to the substance being measured in an analytical procedure.

"Potentiostatic detection" and "potentiostatic detection means" shall refer to the potential of the working electrode with respect to the potential of the reference electrode when the reference potential is maintained at a fixed value and the current through the electrochemical cell (i.e., the sieving matrix) is monitored. The potential of the working electrode determines the reaction taking place at the electrode. Thus, by maintaining the potential, only the desired reaction is allowed to take place.

"Open circuit potential" (also referred to as the equilibrium potential, the rest potential, or the corrosion potential) shall refer to the potential at which there is no current flowing to or from the electrode. This is accomplished by letting the potential of the electrode to float. The reaction at the electrode modifies the open circuit potential and this can be measured. Open circuit potential utilizes two electrodes, the working and counter electrodes.

"Electroactive compounds" and "electrochemically active compounds" shall refer to compounds that have different functional groups which are electrochemically active. Electroactive and electrochemically active compounds are typically, but not always, non-aromatic in nature unless they contain hydroxyl, methoxyl, amine groups or other charged groups. Aliphatic compounds, such as thiols and amines, are electrochemically active.

"Inline" shall refer to a configuration wherein a functional unit (e.g., electrodes) is inserted directly into the process stream. When referring to a device, the functional unit is "inline" when it is part of the device (and not merely attached to the device). When referring to a microfabricated device such as a chip, an inline feature is "on-chip" and is not "off-chip".

"Electrode" shall be refer to an electric conductor through which an electric current enters or leaves, for example, an electrophoresis gel or other medium.

"Working electrode" shall refer to the electrode at which the transfer of a chemical signal into an electric signal takes place. The working electrode should be an ideally polarizable electrode meaning the its potential should not change with the current.

"Reference electrode" shall refer to the electrode that maintains its potential with respect to the solution and, hence, should ideally be non-polarizable. A reference electrode is used in measuring the working electrode potential.

"Counter electrode" shall refer to the electrode that completes the cell circuit.

DESCRIPTION OF THE DRAWINGS

FIGS. 2A, B, C and D show the fabrication flow process. (A) shows the deposition and growth of the dielectric oxide. (B) shows the deposition of base parylene and the patterning of the detection electrodes. (C) shows the patterning of thick photoresist as a sacrificial layer for channel formation. (D) shows the deposition of the top parylene layer, the etching of reservoirs and removal of the sacrificial resistant.

FIGS. 4A and B show (A) a schematic of the micro electrophoresis cell configuration and, (B) a schematic of the potentiostat and electrochemical cell.

FIGS. 5A and B show (A) the potentiostatic detection of FeCA and, (B) open circuit potential measurement for the CE (counter electrode) of FeCA.

FIGS. 6A and B show (A) the potentiostatic detection of CE separation of [a] FeCA and [b] histamine and (B) potentiostatic detection of CE separation of [a] FeCA, [b] histamine and [c] epinephrine.

FIGS. 7A and B show (A) the potentiostatic detection of [a] FeCA, [b] histamine, [c] epinephrine and [d] serotonin and (B) the detection of [a] Fe(bipyridine), [b] Ru(bipyridine), [c] Fe(phenanthroline) and [d] Ru(phenanthroline).

FIGS. 8A and B show (A) detection of [a] $Fe^{2+}$, [b] $Fe^{3+}$ and [c] FeCA and (B) variation of the transit time of the band with electrophoresis field.

DESCRIPTION OF THE INVENTION

The present invention relates to microfabrication and biomolecule separation in microfabricated devices and, in particular, the fabrication of, biomolecule separation with, and detection of biomolecules and chemicals with microfabricated electrophoresis devices. The description of the invention involves I) design and fabrication of microscale electrophoresis devices using silicon, glass and plastic support platforms, II) microfabrication of microdroplet conveying devices, III) channel treatment and, IV) component design.

I. Design of MicroScale Devices

It is present invention contemplates the microscale electrophoresis device is fabricated on a platform. The platform may be made of silicon, glass, plastic, metal, resin ceramics or any compatible substance. In one embodiment, silicon is used for the platform as silicon is a cost-effective material. Silicon is the material used for the construction of computing microprocessors and its fabrication technologies have developed at an unprecedented pace over the past 30 years. While this technology was initially applied to making microelectronic devices, the same techniques are currently being used for micromechanical systems.

Continuous flow liquid transport has been described using a microfluidic device developed with silicon. See J. Pfahler et al., Sensors and Actuators, A21–A23 (1990), pp. 431–434. Pumps have also been described, using external forces to create flow, based on micromachining of silicon. See H. T. G. Van Lintel et al., Sensors and Actuators 15:153–167 (1988). The present invention employs either discrete droplet transport, external forces with pumps and valves or capillary action.

As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. The present invention circumvents some of the compatibility problems with silicon by using it for a platform for building upon.

In one embodiment, the present invention contemplates a silicon platform upon which a base layer is applied after passivation of the surface with an dielectric oxide layer (see, FIG. 2A). Next, parylene is applied and electrodes are to patterned onto the base layer (see, FIG. 2B). A thick photoresist layer is then selectively applied to the base layer as a sacrificial layer for channel formation (see, FIG. 2C). A top layer is then applied to both the base and photoresist layers. Openings are then etched into the top layer to provide access to the capillary reservoir. After etching, the photoresist layer is removed (see, FIG. 2D). Importantly, the fluidic and electronic components of the present invention are designed to be fully compatible in function and construction with the biological and chemical reactions and reagents.

There are a wide variety of isotropic and anisotropic etch reagents, either liquid or gaseous, that can produce channels with well-defined side walls and uniform etch depths. Since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures.

II. Microfabrication of Microdroplet Conveying Devices

The present invention of a microfabricated electrophoresis device with an inline detector may, in one embodiment, be in microdroplet communication with other devices. This section briefly describes these microdroplet conveying devices.

As noted previously, silicon has well-known fabrication characteristics and associated photographic reproduction techniques. The principal modern method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. Of course, the particular fabrication process and sequence used will depend on the desired characteristics of the device. Today, one can choose from among a wide variety of devices and circuits to implement a desired digital or analog logic feature.

III. Channel Treatment

Although the present invention does not require the treatment of channels prior to using the device of the invention, in one embodiment, prior to loading the gel or performing electrophoresis, the channels are preferably treated by washing with base, acid, buffer, water and a hydrophilicity-enhancing compound, followed by a relatively high concentration solution of non-specific protein. In a preferred embodiment, the channels are washed with approximately 100 µl each of the following solutions in series: 0.1N NaOH; 0.1N HCl; 10 mM Tris-HCl (pH 8.0), deionized $H_2O$, Rain-X Anti-Fog (a hydrophilicity-enhancing compound commercially available from Unelko Corp., Scottsdale, Ariz.), and 500 µg/µl bovine serum albumin (non-specific protein commercially available in restriction enzyme grade from GIBCO-BRL).

IV. Component Design

Figure 1:
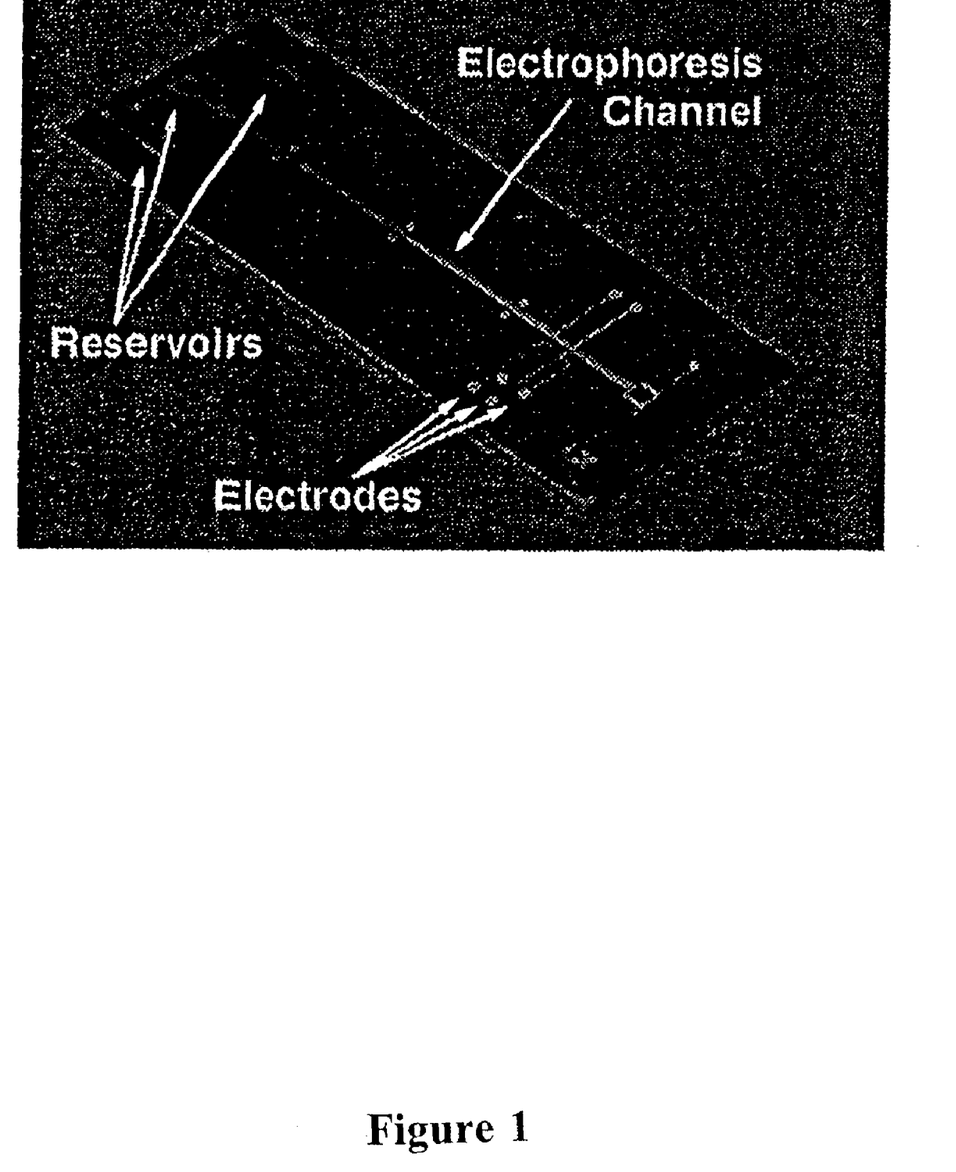
FIG. 1 shows an optical micrograph of the electrophoresis device with integrated electrochemical detection and with a 2 cm long separation channel.

The present invention contemplates one or more gel electrophoresis modules as an integral component of the microscale device. FIG. 1 is an optical micrograph of the electrophoresis device with the integrated electrochemical detection electrodes and a 2 cm long separation channel.

Figure 7:
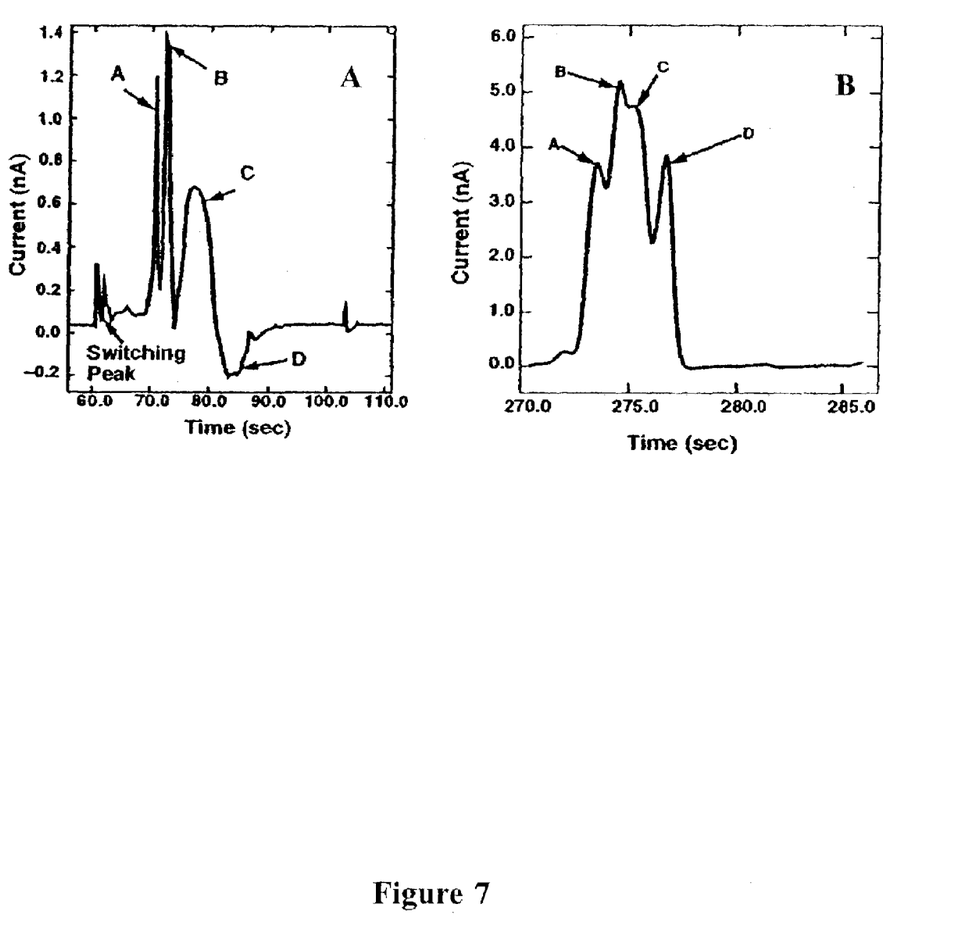

To demonstrate that inline detection can operate in micron-diameter capillary electrophoresis channels, the devices were fabricated using the procedure described in Example 1. Polyacrylamide gel electrophoresis of a complex protein mixture is shown in FIGS. 7A and 7B. The high resolution of the detector (in this case using open circuit potential; OCP) allowed the detection of the four peptides; FeAC, histamine, epinephrine and serotonin.

The present invention contemplates an electrophoresis unit that integrates a microfabricated channel and an inline electronic detector. The channel is constructed by layering a top layer of, for example, parylene over a photoresist layer of the prescribed size for the gel.

Parylene is a conformal protective polymer coating material utilized to uniformly protect any component configuration on such diverse substrates as metal, glass, paper, resin, plastic, ceramic, ferrite and silicon. Because of its unique properties, Parylene conforms to virtually any shape, including sharp edges, crevices, points (including the photoresist layer of the present invention); or flat and exposed internal surfaces.

After etching openings for liquid flow into the top layer, the photoresist layer is removed leaving a channel for capillary electrophoresis. Etching is done using an oxygen plasma reactive ion etching (RIE) procedure, a technique well know in the field of integrated circuit manufacture (Brake, M. L., et al., "Reactive ion etching in the gaseous electronics conference RF reference cell", *J. Res. Natl. Inst. Stand. Technol.*, 100:441–448, 1995). Reactive ion etching (RIE) employs reactive species in the plasma to selectively remove materials. Gases such as $SF_6$, $CHF_3$, and $O_2$ are commonly used. The etching selectivity is the result of the etching process being primarily a chemical process. Etching products remain in gas phase and are pumped out of the system immediately. The ion energy does play a role in the etching process, giving more flexibility (or complexity) to the process.

In the present invention the configuration of the etching in the top layer is patterned by depositing on the surface an etch-sensitive material (phosphosilicate glass, $SiO_2.P_x$) with a thickness equivalent to the desired channel height. An overlay of deposited material completely covers the sacrificial material with the exception of small access holes on the top or sides. A selective liquid etch removes the sacrificial photoresist layer material, but not the overlay (top layer) or the underlay (base layer).

EXPERIMENTAL

The following examples serve to illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); gm (grams); mg (milligrams); μg (micrograms); L (liters); ml (milliliters); μl (microliters); cm (centimeters); mm (millimeters); μm (micrometers); nm (nanometers); ° C. (degrees Centigrade); Ci (Curies); MW (molecular weight); OD (optical density); EDTA (ethylenediamine-tetracetic acid); PAGE (polyacrylamide gel electrophoresis); UV (ultraviolet); V (volts); W (watts); mA (milliamps); bp (base pair); CPM (counts per minute).

EXAMPLE 1

Device structure and fabrication. FIG. 1 shows the optical micrograph of the electrophoresis device with inline electrochemical detection. The detection system consists of three electrodes, namely working, counter and reference electrodes, as seen in the micrograph.

Figure 2:
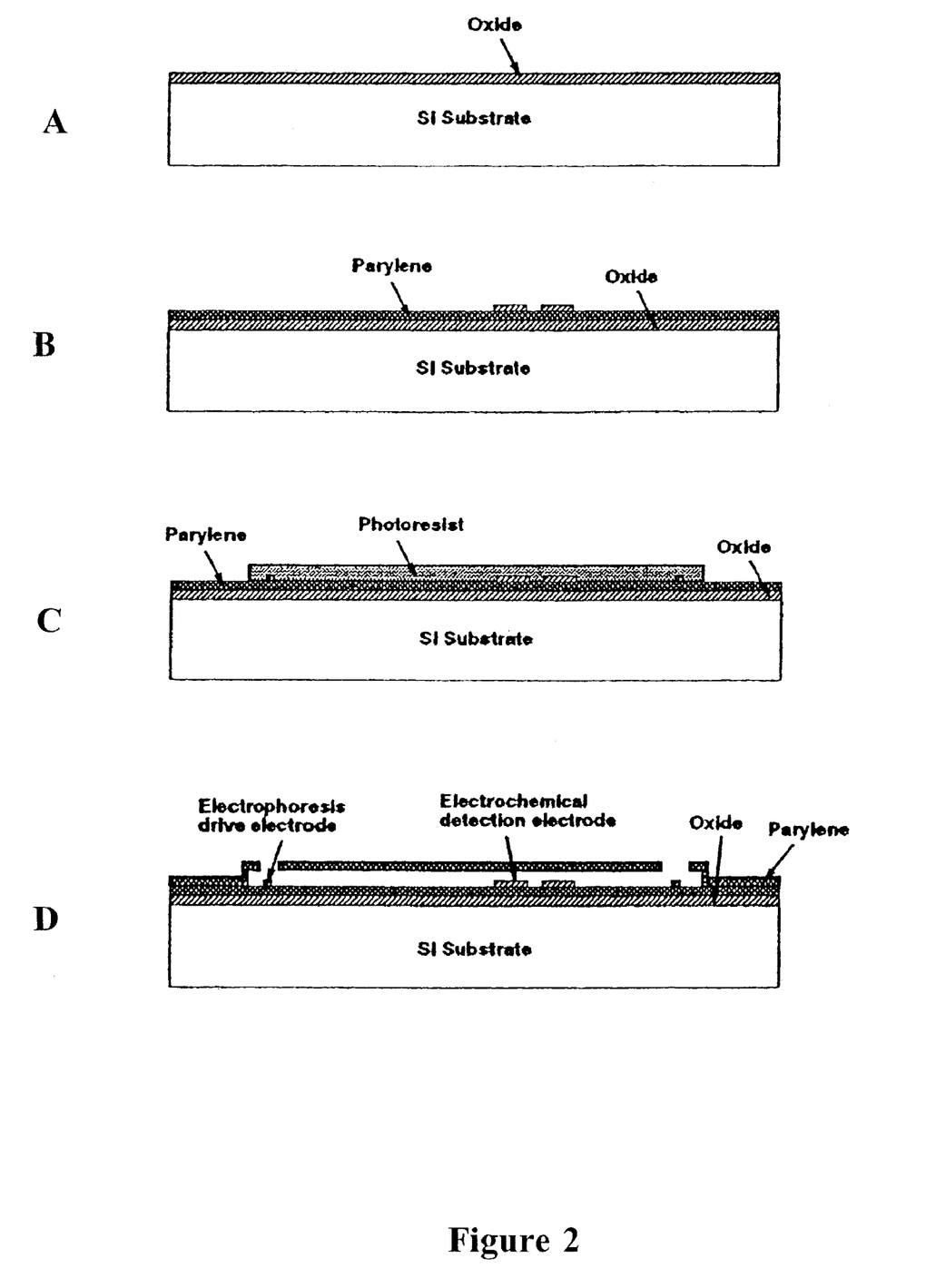

FIG. 2 shows the simple process flow for the fabrication of the device. The electrophoresis channels are surface micromachined of polymer material (Parylene), using photoresist as a sacrificial layer (Man, P. F., el al., "Microfluidic capillaries on silicon: A new inexpensive technology for bioanalysis chips", *IEEE MEMS* 1997 *Conference, Nagoya Japan*, pp. 311–316, 1997). Fabrication is a simple 4 mask process. The starting substrate can be of any material (silicon, glass, plastics), and provides only a mechanical platform on which the microsystem is built. Here we use silicon as the substrate material. A passivation layer of thermal oxide (0.2 μm) was next grown on the wafer under wet, trichloroethane (TCA) conditions at 900° C. A parylene base layer (5 μm) was deposited using chemical vapor deposition on the oxide which provides good adhesion. Next, a 0.1 μm thick gold electrophoresis electrodes and detection electrodes war patterned. The sacrificial photoresist is then patterned using a 20 μm thick layer of AZ9260 (Clariant). The top layer of the channel is then formed by depositing a 5 μm thick parylene layer. Adhesion of this layer to the base parylene layer is assisted by a short oxygen plasma RIE using a thick photoresist mask. The channel reservoir openings as well as the electrode pad openings are etched at this stage. Photo-definable silicone rubber rings can be patterned around the reservoirs to increase the holding capacity.

In the device tested, this step was avoided out of convenience and the rings were applied by hand. The wafer was diced using a diamond tip saw. The devices were then released in acetone for 20 hours followed by an IPA rinse and a $N_2$ dry.

EXAMPLE 2

Separation conditions. Separations were performed in these devices using a sieving matrix consisting of 0.5% (w/w) hydroxyethylcellulose (HEC) (Polysciences, Inc. Warrington, Pa.; MW 90000–105000) and 0.1×Tris/Boric Acid/EDTA buffer (Sigma Chemical CO., St. Louis, Mo.). Approximately 5 ul of the buffer solution is loaded in one reservoir and allowed to fill the entire channel by capillary action. The remaining reservoirs are also filled with approximately 5 ul of buffer solution. The channel was pre-electrophoresed at 150 V/cm for 5 minutes. This was found to concentrate the HEC in the separation column to more than 0.5% resulting in a higher resolving power of the gel. A 0.2 ug/ul sample of probe solution was loaded into the injection reservoir. The sample was cross injected using a pinched injection scheme.

Instrumentation. A stereo microscope (Olympus SZX12) equipped with a fluorescence illuminator (100 W Mercury lamp illuminator) was used to observe the separations. A high sensitive potentiostat specially designed (Gamry instruments, PA) was used to measure the output of the detection electrodes and set different modes of operation of the electrodes.

Detection system design. EC detection system consists of three electrodes, the working, counter and reference electrodes. The working electrode (WE) being the electrode at which the transfer of a chemical signal into an electrical signal takes place is made of 1000 nm thick Au, 10 um in width and 160 um in length. Au was chosen as the working electrode as it provides a high hydrogen over potential which aids in the prevention of bubble generation over a greater range of potential differences. The working electrode should be an ideally polarizable electrode, meaning that its potential should not change with the current. The reference electrode (RE) maintains its potential with respect to the solution and hence should ideally be non-polarizable. Typically Ag/AgCl is used as the RE because of its near ideal non-polarizable behavior. In micro EC cells, since the amount of current handled is very small, metals can be used for the RE if its surface area is made much larger [than] the WE area. A large area metal RE is acceptable because the effect of current variation on potential is weak. In our device, all the electrodes are made with Au, to simplify the fabrication process.

Figure 3:
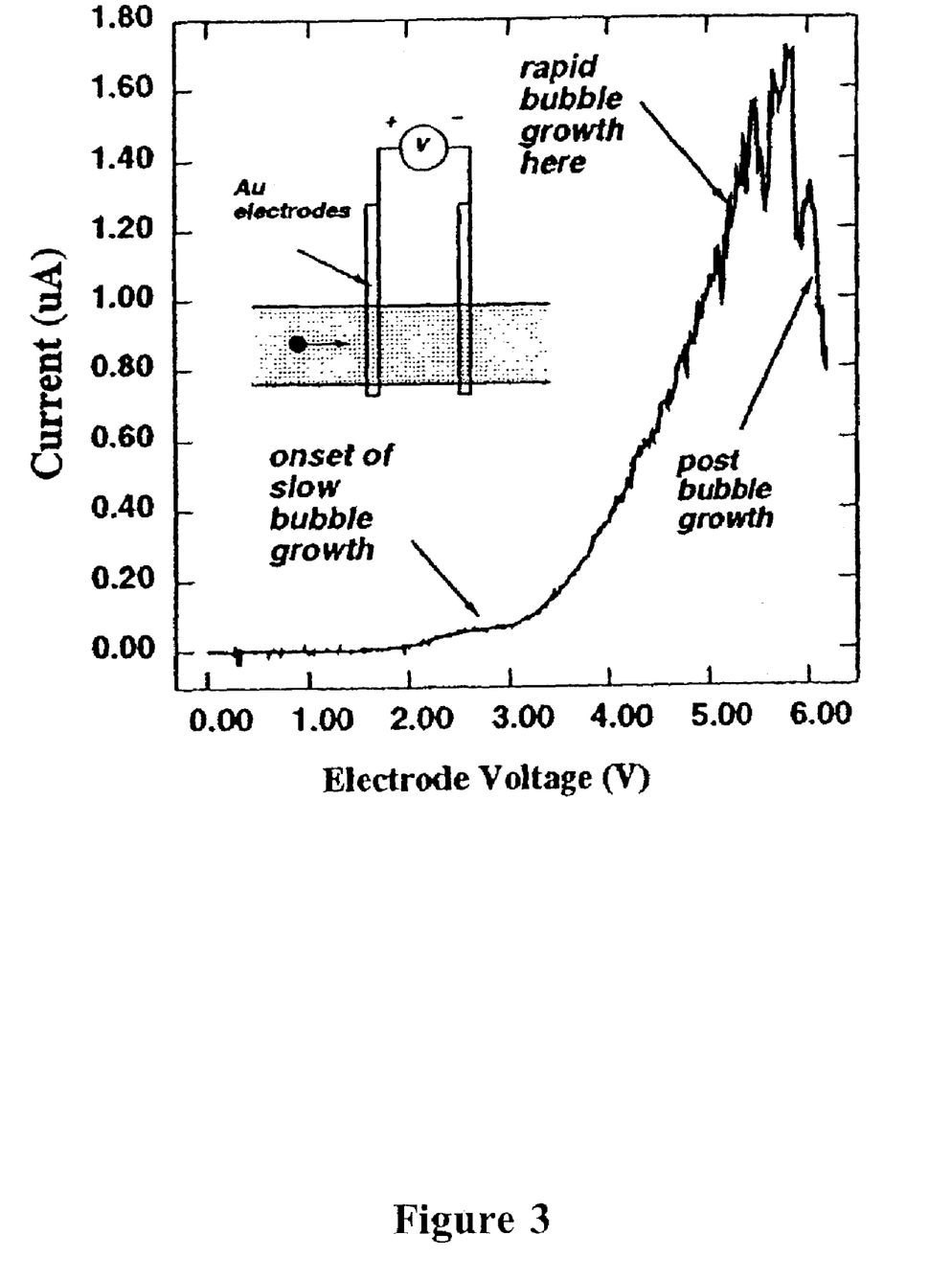
FIG. 3 shows the current voltage characteristics of bubble generation at an electrode.
Figure 4:
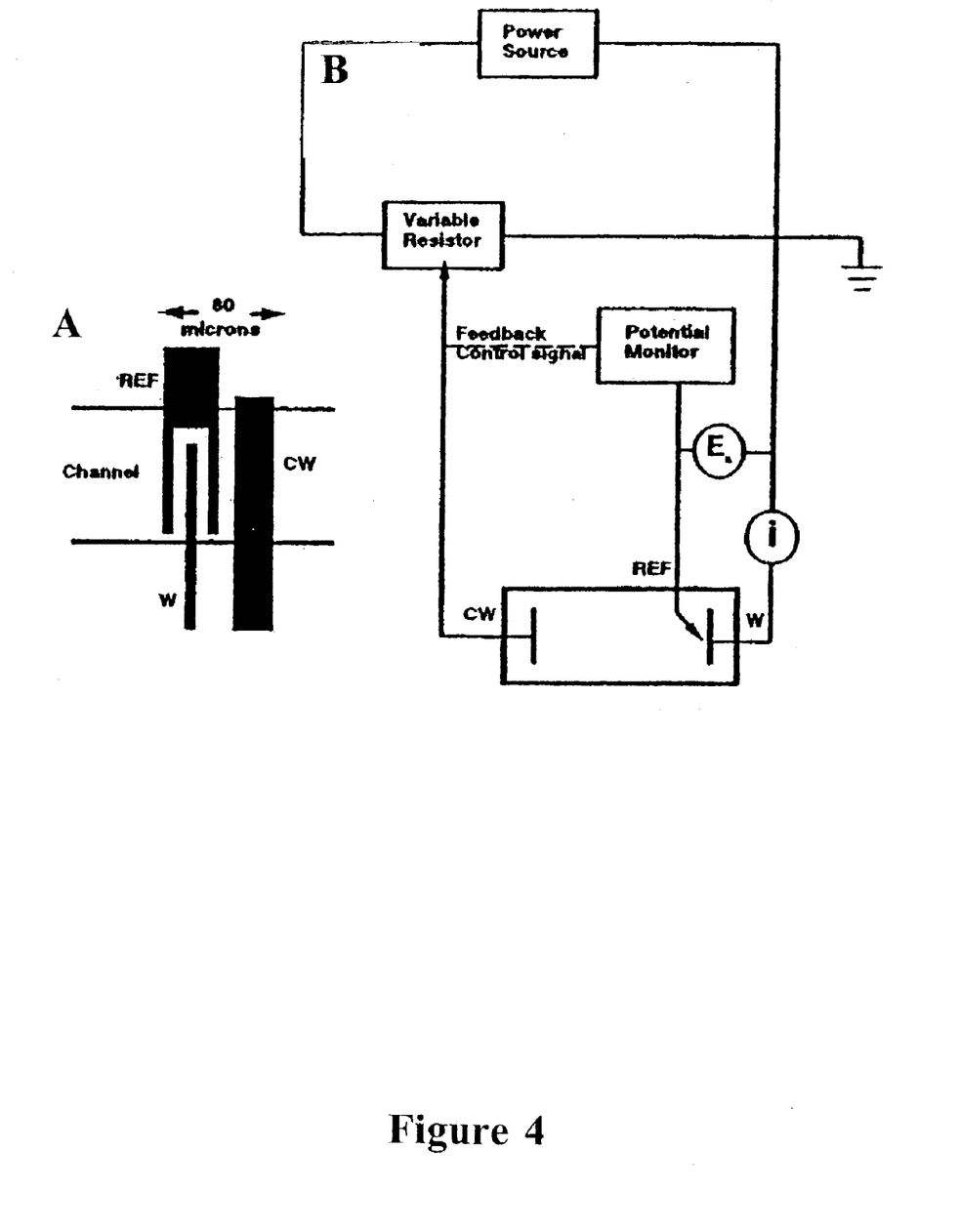

When an electrode is floating it takes up the potential of the solution. In a EC channel there is a gradient of potential equal to the electric field applied. Thus, if the distance between the WE and the CE electrodes is sufficiently large, that the potential difference between them will be greater than 1.2 V, the theoretical potential for gas evolution. Under this condition if two electrodes are connected, gas evolution will occur. The potential effect of potential difference on the gas evolution is shown in FIG. 3. In order to avoid bubble generation the entire detection system was designed to be less that 80 um in width. The RE was also designed to envelope the WE as shown in FIG. 4A, so that the region around the WE is maintained at a stable potential. This helps in reducing noise in the detection signal as then the entire electrochemical cell floats with a single solution potential. A typical potentiostat-electrochemical cell system is shown in FIG. 4B.

Here the working electrode is grounded and the potential is applied to the counter electrode to maintain a potential difference across the cell. However, when this configuration is used along an electrophoresis separation setup, the electrophoresis and detection systems are coupled due to the common ground. This causes the detection electrode (DE) to short the electrophoresis field in the channel and, hence, results in gas evolution. This is prevented in our potentiostat by designing the potentiostat with an ungrounded WE. This decouples the electrophoresis and detection systems and the electrodes float with the solution potential. Hence, the electrode system was designed to have as small a width as possible along the electrophoresis field, so that the variation in potential between the electrodes are small and the entire system floats at the same solution potential. The floating potential of the electrode causes drift in electrode signal, but because the drift is slow, it does not affect the detection limit.

EXAMPLE 3

Figure 5:
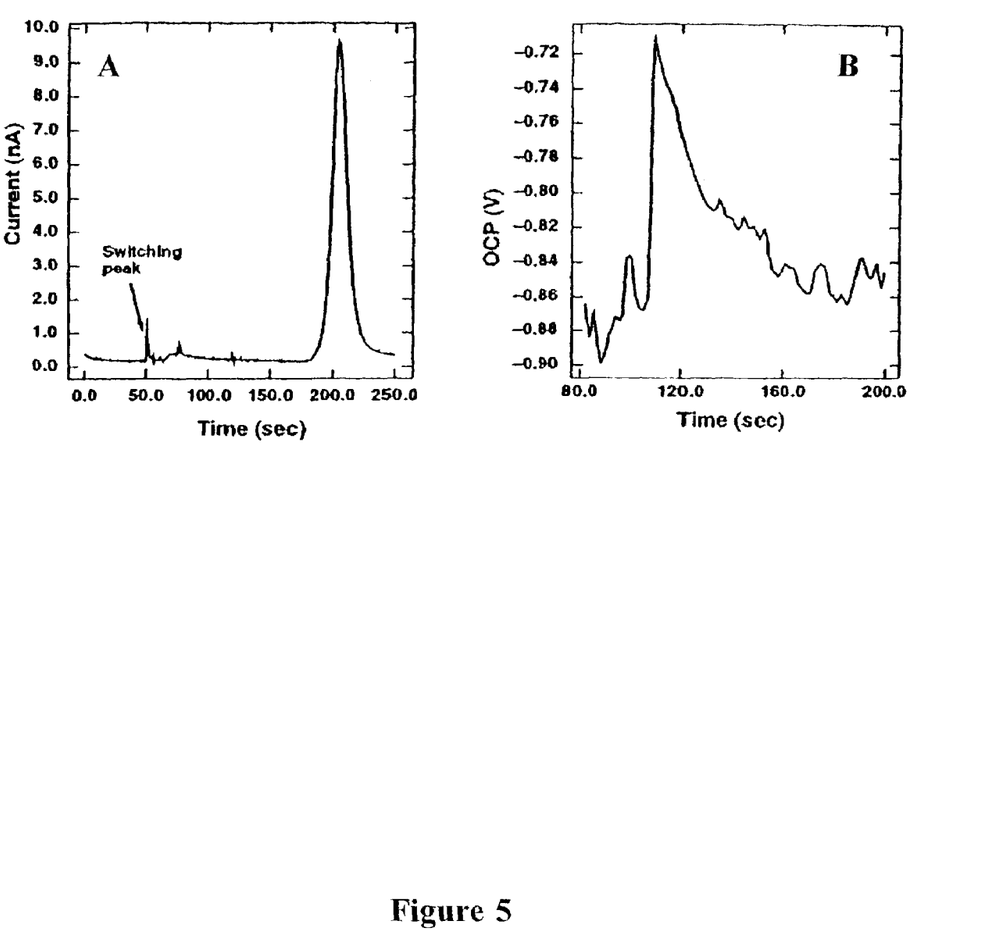

Electrochemical detection. Electrochemical detection can be achieved by two method. In potentiostatic detection, the potential of the WE with respect to the RE is maintained at a fixed value and the current through the electrochemical cell is monitored. The potential of the WE determines the reaction taking place at the electrode. Thus, by maintaining the potential only the desired reaction is allowed to take place. The peak in the current then indicates the occurrence of the desired reaction. In open circuit potential (OCP) mode, the potential of the electrode is allowed to float and is measured periodically. The reaction occurring at the surface of the electrode modifies the OCP of the electrode and this can be monitored. Potentiostatic mode utilized three electrode configuration and hence has lesser noise compared to OCP mode as seen in FIG. 5.

FIG. 5A shows the potentiostatic detection of a single electrochemically active compound. The compound chosen was Ferrocene di carboxylic acid (FeCA). It has a reduction potential of 0.5 V, as measured from CV measurements. The potential difference between the WE and RE was maintained at 0.8 V in all the experiments. The response of the system is affected by the switching of potentials in the electrophoresis channel from the injection to separation mode in pinched type injection scheme. Therefore, we see a jump in the current at t=60 seconds when the potentials are switched.

FIG. 5B shows the OCP mode detection of the same compound. The signal is affected by variation of the electric field along the channel. Thus, the noise level is much higher. The decay time of the signal is also higher. In the case of potentiostatic detection the system is brought back to equilibrium by imposition of a feedback in potential to the WE. However, in OCP detection, no external input is used to restore the equilibrium after the influence of the electroactive compound. This accounts for the higher decay time.

The noise levels in the two different modes of operation were estimated by performing the experiments without any analyte present. The separation field was 150 V/cm. The buffer and gel concentration were the same as in the other experiments. In case of the potentiostatic mode, the average rms noise level was 0.7 pA on a signal level of 5 nA. There was a drift in the signal of 1.18 pA/s. In the OCP mode of operation the noise level was 9.1 mV on a signal level of 800 mV and the drift was 0.22 mV/s. The S/N ratio for the potentiostatic mode was higher than for OCP mode due to the potential feedback mechanism and the three electrode configuration. The minimum detectable signal (assuming S/N=2) was 14.5 amol.

Figure 6:
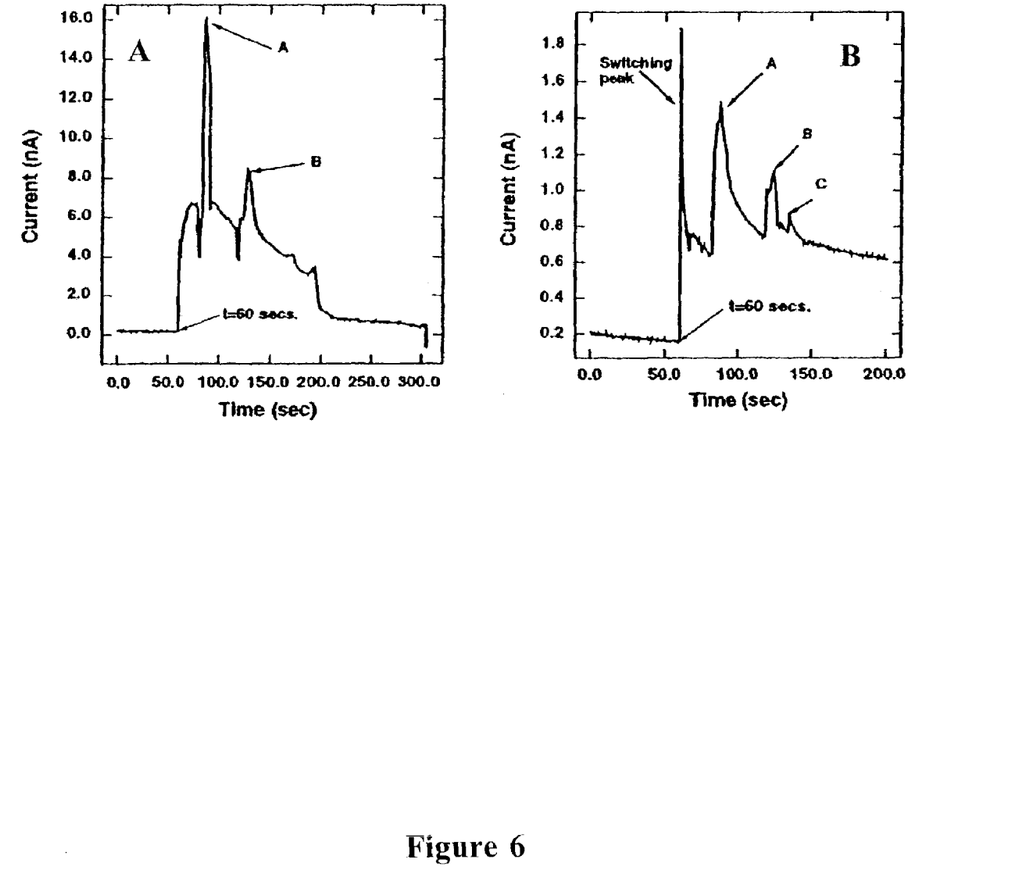

FIGS. 6A and B shows the detection of two and three electroactive compounds. In these plots the peak heights are approximately in the ratio of their concentration.

FIG. 7A shows detection of four electroactive compounds. The reaction of serotonin is a reduction reaction leading to a dip in the current observed. Thus, the type of reaction can also be deducted from this data. FIG. 7B shows the separation of compounds which can be used as electrochemical tags to DNA. These compounds are believed to attach themselves to the minor groove of the double stranded DNA (Rodriguez, M. and A. J. Bard, "Electrochemical studies of the interaction of metal chelates with DNA", *Anal. Chem.*, 62:2658–2662, 1997). Replacing the metal atoms in the compounds and utilizing the properties of potential discrimination of chemical species, color coding of DNA can be achieved.

Figure 8:
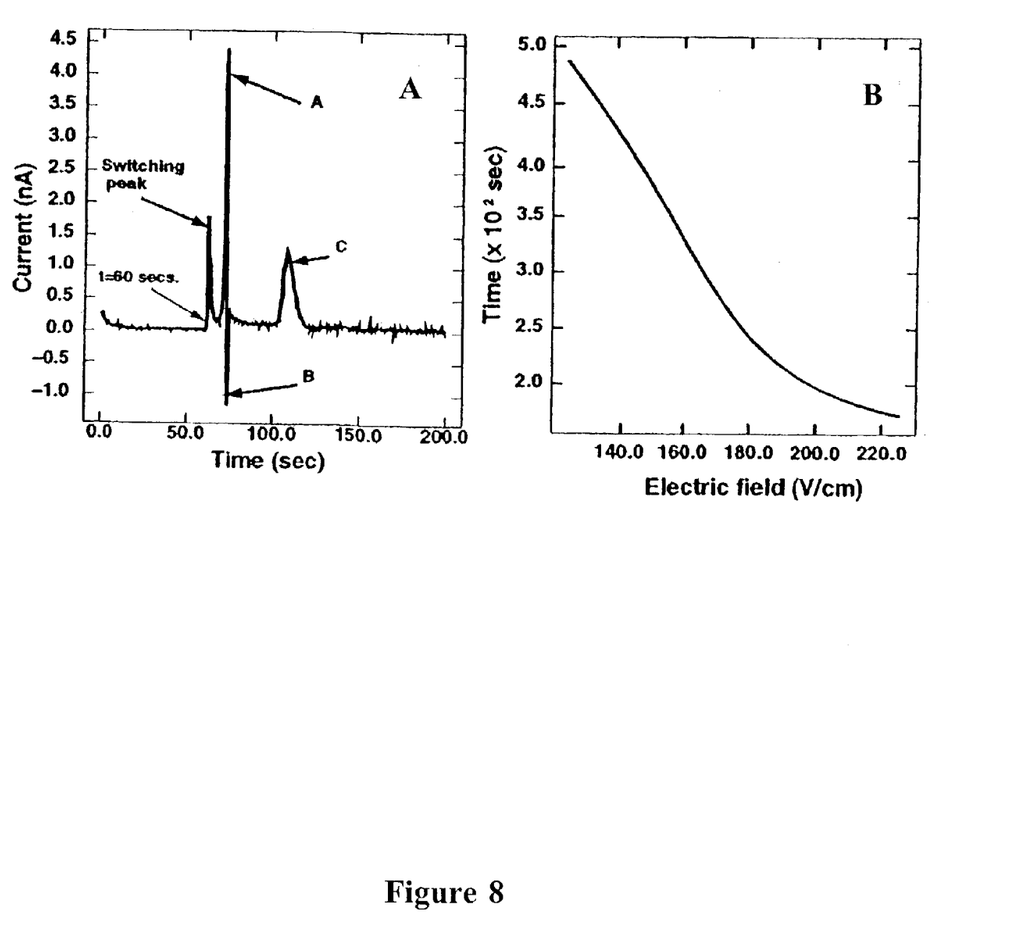

FIG. 8A shows the oxidation and reduction occurring at the WE and CE. Analyte consists of ferrocyanide ($Fe(CN)_6^{2+}$) and FeCA. The ferrocyanide undergoes oxidation at the WE at a potential of 0.2 V, and it is transformed into ferricyanide. This ferricyanide is then reversibly converted into ferrocyanide at the CE which is downstream to the WE. FIG. 8B shows the variation in electrophoresis mobility of FeCA with the variation in the electric field. The result is consistent with that observed for gel electrophoresis in (Grossman, P. D. and J. C. Colburn, *Capillary Electrophoresis*, Academic Press, 1992).

From the foregoing, it is clear that the present invention provides methods and materials for the production and utilization of a small-scale, electrophoretic separation system based utilizing a novel, inexpensive fabrication system and an inline detection system giving superior resolution at a reduced cost.

We claim:
1. A device, comprising:
   i) a substrate comprising one or more microchannels;
   ii) a sieving matrix disposed within said one or more microchannels;
   iii) one or more reservoirs in fluidic communication with said one or more microchannels; and iv) an inline electrochemical detector comprising a working electrode and a counter electrode, wherein said working electrode is substantially surrounded by a reference electrode positioned within at least one of said one or more microchannels.

2. The device of claim 1, wherein said substrate comprises a material selected form the group consisting of silicon, glass, plastic, metal, resin, ceramic or quartz.

3. The device of claim 1, wherein said each of said electrodes comprises a material selected from the group consisting of gold, silver/silver chloride, carbon, palladium or platinum.

4. A method comprising:
i) providing;
   a) the device of claim 1, and
   b) a fluid comprising biomolecules;
ii) applying said fluid to said sieving matrix; and
iii) detecting said biomolecules. wherein said detecting comprises an electric field variation selected from the group consisting of an electrical potential and an electrical current.

5. The method of claim 4, wherein said electric field variation identifies at least two different said biomolecules.

6. The method of claim 4, wherein said electric potential is less than 1.2 V.

7. The method of claim 4, wherein said biomolecules comprise a functional group selected from the group consisting of hydroxyl, carboxyl, methoxyl, amine, and thiol.

8. A method comprising:
providing;
   a) the device of claim 1, and
   b) a fluid comprising biomolecules;
ii) applying said fluid to said sieving matrix under conditions such that said biomolecules are separated from one another; and
iii) detecting said biomolecules. wherein said detecting comprises an electric field variation selected from the group consisting of an electrical potential and an electrical current.

9. The method of claim 8, wherein said electric field variation identifies at least two different said biomolecules.

10. The method of claim 8, wherein said electric potential is less than 1.2 V.

11. The method of claim 8, wherein said biomolecules comprise a functional group selected from the group consisting of hydroxyl, carboxyl, methoxyl, amine, and thiol.

* * * * *

UNITED STATES PATENT AND TRADEMARK OFFICE
CERTIFICATE OF CORRECTION

| | | |
|---|---|---|
| PATENT NO. | : 7,125,478 B2 | Page 1 of 1 |
| APPLICATION NO. | : 10/342935 | |
| DATED | : October 24, 2006 | |
| INVENTOR(S) | : Ponnambalam Selvaganapathy et al. | |

It is certified that error appears in the above-identified patent and that said Letters Patent is hereby corrected as shown below:

Col. 1, lines 8-9
Please insert the following text prior to the "FIELD OF THE INVENTION"

This invention was made with government support under HG 001984-01 awarded by the National Institutes Of Health. The government has certain rights in this invention.

Signed and Sealed this

Sixth Day of March, 2007

JON W. DUDAS
*Director of the United States Patent and Trademark Office*